(12) United States Patent
Padmanabhan et al.

(10) Patent No.: US 10,471,082 B2
(45) Date of Patent: Nov. 12, 2019

(54) FLAVIVIRUS PROTEASE INHIBITORS

(71) Applicant: GEORGETOWN UNIVERSITY, Washington, DC (US)

(72) Inventors: Radhakrishnan Padmanabhan, Bethesda, MD (US); Tadahisa Teramoto, Potomac, MD (US); Mark Manzano, Chicago, IL (US)

(73) Assignee: Georgetown University, Washington, DC (US)

( * ) Notice: Subject to any disclaimer, the term of this patent is extended or adjusted under 35 U.S.C. 154(b) by 686 days.

(21) Appl. No.: 14/437,434

(22) PCT Filed: Oct. 23, 2013

(86) PCT No.: PCT/US2013/066380
§ 371 (c)(1),
(2) Date: Apr. 21, 2015

(87) PCT Pub. No.: WO2014/066502
PCT Pub. Date: May 1, 2014

(65) Prior Publication Data
US 2015/0272976 A1   Oct. 1, 2015

Related U.S. Application Data (60) Provisional application No. 61/717,221, filed on Oct. 23, 2012.

(51) Int. Cl.
| | | |
|---|---|---|
| *A61K 31/7032* | (2006.01) | |
| *A61K 31/519* | (2006.01) | |
| *A61K 31/12* | (2006.01) | |
| *A61K 31/352* | (2006.01) | |
| *A61K 31/415* | (2006.01) | |
| *A61K 31/426* | (2006.01) | |
| *A61K 31/44* | (2006.01) | |
| *A61K 31/7034* | (2006.01) | |
| *A61K 31/4178* | (2006.01) | |
| *A61K 45/06* | (2006.01) | |

(52) U.S. Cl.
CPC .......... *A61K 31/7032* (2013.01); *A61K 31/12* (2013.01); *A61K 31/352* (2013.01); *A61K 31/415* (2013.01); *A61K 31/4178* (2013.01); *A61K 31/426* (2013.01); *A61K 31/44* (2013.01); *A61K 31/519* (2013.01); *A61K 31/7034* (2013.01); *A61K 45/06* (2013.01); *Y02A 50/385* (2018.01); *Y02A 50/389* (2018.01); *Y02A 50/393* (2018.01)

(58) Field of Classification Search
None
See application file for complete search history.

(56) References Cited

U.S. PATENT DOCUMENTS

| | | |
|---|---|---|
| 2010/0041732 A1 | 2/2010 | Caldwell et al. |
| 2012/0022046 A1 | 1/2012 | Byrd et al. |
| 2012/0208204 A1 | 8/2012 | Baldwin et al. |

FOREIGN PATENT DOCUMENTS

| | | |
|---|---|---|
| EP | 2185570 B1 | 3/2014 |
| WO | 2009023718 A2 | 2/2009 |
| WO | WO 2010/039538 A2 * | 4/2010 |

OTHER PUBLICATIONS

Carson, P. J. et al., Clinical Infectious Diseases, "Long-Term Clinical and Neuropsychological Outcomes of West Nile Virus Infection", 2006, vol. 43, pp. 723-730.*
Factor, Stewart A., Parkinson's Disease Foundation, "Treating the "off" periods in Parkinson's", 2003, also available at http://www.pdf.org/en/fall03_periods; last viewed Oct. 5, 2016.*
Pahwa, R. et al., American Academy of Neurology, "Practice Parameter: Treatment of Parkinson disease with motor fluctuations and dyskinesia", 2006, vol. 66, pp. 983-995.*
"Prevent", Wordnet Search 3.0, also available at http://wordnet.princeton.edu; last viewed Nov. 14, 2007.*
The CCP4 suite: programs for protein crystallography, CCP4, ActaCrystallogr. D. Biol. Crystallogr., vol. 50, 1994, pp. 760-763.
Aertgeerts et al., Crystal structure of human dipeptidyl peptidase IV in complex with a decapeptide reveals details on substrate specificity and tetrahedral intermediate formation, Protein Sci., vol. 13, No. 2, Feb. 2004, pp. 412-421.
Aertgeerts et al., N-linked glycosylation of dipeptidyl peptidase IV (CD26): Effects on enzyme activity, homodimer formation, and adenosine deaminase binding, Protein Sci., vol. 13, No. 1, 2004, pp. 145-154.
Aleshin et al., Structural evidence for regulation and specificity of flaviviral proteases and evolution of the Flaviviridae fold, Protein Sci., vol. 16, No. 5, May 2007, pp. 795-806.
Aravapalli et al., Inhibitors of Dengue virus and West Nile virus proteases based on the aminobenzamide scaffold, Bioorg Med Chem., vol. 20, No. 13, Jul. 1, 2012, pp. 1-22.
Arenal et al., Reaction of 5(4h)-thiazolones with diazomethane, Tetrahedron, vol. 39, No. 8, 1983, pp. 1387-1393.
Assenberg et al., Crystal structure of a novel conformational state of the flavivirus NS3 protein: implications for polyprotein processing and viral replication, J Virol, vol. 83, No. 24, Dec. 2009, pp. 12895-12906.
Audisio, A simple synthesis of functionalized 3- bromocoumarins by a one-pot three-component reaction, European Journal of Organic Chemistry, vol. 2010, No. 6, Feb. 2010, pp. 1046-1051.

(Continued)

*Primary Examiner* — Shaojia A Jiang
*Assistant Examiner* — Bahar Craigo
(74) *Attorney, Agent, or Firm* — Kilpatrick Townsend & Stockton LLP (57) ABSTRACT

Methods of treating or preventing a *Flavivirus* infection in a subject are provided. The methods comprise administering to the subject a therapeutically effective amount of a *Flavivirus* inhibitor, e.g., a *Flavivirus* protease inhibitor. These methods are useful in treating and/or preventing *Flavivirus* infections such as, for example, West Nile Virus, Dengue Virus, and Japanese Encephalitis Virus. Methods of inhibiting a *Flavivirus* protease in a cell are also provided.

14 Claims, 4 Drawing Sheets

(56) References Cited

OTHER PUBLICATIONS

Chandramouli et al., Serotype-specific structural differences in the protease-cofactor complexes of the dengue virus family, J Virol., vol. 84, No. 6, Mar. 2010, pp. 3059-3067.
Clum et al., Cotranslational membrane insertion of the serine proteinase precursor NS2B-NS3(Pro) of dengue virus type 2 is required for efficient in vitro processing and is mediated through the hydrophobic regions of NS2B, J Biol Chem., vol. 272, No. 49, Dec. 5, 1997, pp. 30715-30723.
Cregar-Hernandez et al., Small molecule pan-dengue and West Nile virus NS3 protease inhibitors, Antivir Chem Chemother, vol. 21, No. 5, May 12, 2011, pp. 209-218.
De Clercq, The design of drugs for HIV and HCV, Nature Reviews Drug Discovery, vol. 6, No. 12, Dec. 2007, pp. 1001-1018.
De Mora et al., Evidence of diversification of dengue virus type 3 genotype III in the South American region, Archives of Virology, vol. 154, No. 4, Apr. 2009, pp. 699-707.
Dou et al., Design, Synthesis and In Vitro Evaluation of Potential West Nile Virus Protease Inhibitors Based on the 1-Oxo-1, 2, 3, 4-tetrahydroisoquinoline and 1-Oxo-1, 2-dihydroisoquinoline Scaffolds, J Comb Chem., vol. 12, No. 6, Nov. 8, 2010, pp. 836-843.
Ekonomiuk et al., Discovery of a Non-Peptidic Inhibitor of West Nile Virus NS3 Protease by High-Throughput Docking, PLoS Negl Trop Dis., e356, vol. 3. No. 1, Jan. 2009, pp. 1-9.
Erbel et al., Structural basis for the activation of flaviviral NS3 proteases from dengue and West Nile virus, Nature Structural & Molecular Biology, vol. 13, Mar. 12, 2006, pp. 372-373.
Ezgimen et al., Characterization of the 8-hydroxyquinoline scaffold for inhibitors of West Nile virus serine protease, Antiviral Res., vol. 94, No. 1, Apr. 2012, pp. 18-24.
Ezgimen et al., Effects of Detergents on the West Nile virus Protease Activity, Bioorg Med Chem., vol. 17, No. 9, May 1, 2009, pp. 3278-3282.
Feng et al., A high-throughput screen for aggregation-based inhibition in a large compound library, J Med Chem., vol. 50, No. 10, Apr. 21, 2007, pp. 2385-2390.
Fioravanti et al., Facile and Highly Stereoselective One-Pot Synthesis of Either (E)- or (Z)-Nitro Alkenes, Org. Lett., vol. 10. No. 7, Feb. 27, 2008, pp. 1449-1451.
Ganesh et al., Identification and Characterization of Nonsubstrate Based Inhibitors of the Essential Dengue and West Nile Virus Proteases, Bioorganic and Medicinal Chemistry vol. 13, No. 1, Jan. 3, 2005, pp. 257-264.
Gwaltney et al., Design and synthesis of potent, selective, and orally efficacious DPP4 inhibitors accelerated by highthroughput structural biology, 30th National Medicinal Chemistry Symposium, University of Washington, Seattle, Jun. 25-29, 2006, 1 page.
Hopkins et al., Ligand efficiency: a useful metric for lead selection, Drug Discovery Today, vol. 9, No. 10, May 15, 2004, pp. 430-431.
Imrie et al., Homology of complete genome sequences for dengue virus type-1, from dengue-fever- and dengue-haemorrhagic-fever-associated epidemics in Hawaii and French Polynesia, Ann Trop Med Parasitol, vol. 104, No. 3, Apr. 2010, pp. 225-235.
Johnston et al., HTS identifies novel and specific uncompetitive inhibitors of the two-component NS2B-NS3 proteinase of West Nile virus, Assay Drug Dev Technol, vol. 5, No. 6, Dec. 2007, pp. 737-750.
Laughlin et al., Dengue Research Opportunities in the Americas, Journal of Infectious Diseases Advance Access, vol. 206, No. 7, Jul. 9, 2012, pp. 1121-1127.
Leslie, Joint CCP4 + ESF-EAMCB Newsletter on Protein Crystallography, Apr. 1992.
Mcree, XtalView/Xfit—A versatile program for manipulating atomic coordinates and electron density, Journal of Structural Biology, vol. 125, No. 2-3, Apr. 1999, pp. 156-165.
Meanwell, Synopsis of Some Recent Tactical Application of Bioisosteres in Drug Design, J. Med. Chem., vol. 54, No. 8, Mar. 17, 2011, pp. 2529-2591.

Melagraki et al., Ligand and Structure Based Virtual Screening Strategies for Hit-Finding and Optimization of Hepatitis C Virus (HCV) Inhibitors, Curr Med Chem., vol. 18, No. 17, 2011, pp. 2612-2619.
Mueller et al., Characterization of the West Nile virus protease substrate specificity and inhibitors, The International Journal of Biochemistry and Cell Biology, vol. 39, No. 3, 2007, pp. 606-614.
Mueller et al., Identification and Biochemical Characterization of Small-Molecule Inhibitors of West Nile Virus Serine Protease by a High-Throughput Screen, Antimicrobial Agents and Chemotherapy, vol. 52, No. 9, 2008, pp. 3385-3393.
Nitsche et al., Arylcyanoacrylamides as inhibitors of the Dengue and West Nile virus proteases, Bioorganic & Medicinal Chemistry, vol. 19, No. 24, Dec. 15, 2011, pp. 7318-7337.
Noble et al., Ligand-Bound Structures of the Dengue Virus Protease Reveal the Active Conformation, J Virol., vol. 86, No. 1, Jan. 2012, pp. 438-446.
Padmanabhan et al., Translation and processing of the dengue virus polyprotein, In K. A. Hanley and S. C. Weaver (ed.), Frontiers in Dengue Virus Research. Caister Academic Press, Norfolk, U.K, 2010, pp. 14-33.
International Application No. PCT/US2013/066380, International Preliminary Report on Patentability dated May 7, 2015, 8 pages.
International Application No. PCT/US2013/066380, International Search Report and Written Opinion, dated May 13, 2014, 13 pages.
Robin et al., Structure of West Nile Virus NS3 Protease: Ligand Stabilization of the Catalytic Conformation, Journal of Molecular Biology, vol. 385, No. 5, Feb. 6, 2009, pp. 1568-1577.
Sampath et al., Molecular targets for flavivirus drug discovery, Antiviral Res., vol. 81, No. 1, Jan. 2009, pp. 6-15.
Skubák et al., Extending the resolution and phase-quality limits in automated model building with iterative refinement, Acta Crystallogr D Biol Crystallogr, vol. 61 ,, Dec. 2005, pp. 1626-1635.
Su et al., Structural basis for the inhibition of RNase H activity of HIV-1 reverse transcriptase by RNase H active site-directed inhibitors, J Virol., vol. 84, No. 15, Aug. 2010, pp. 7625-7633.
Su et al., Substituted tetrahydroquinolines as potent allosteric inhibitors of reverse transcriptase and its key mutants, Bioorganic & Medicinal Chemistry Letters, vol. 19, No. 17, Sep. 1, 2009, pp. 5119-5123.
Thomsen et al., MolDock: a new technique for high-accuracy molecular docking, J. Med. Chem., vol. 49, No. 11, Apr. 29, 2006, pp. 3315-3321.
Tiew et al., Inhibition of Dengue virus and West Nile virus proteases by click chemistry-derived benz[d]isothiazol-3(2H)-one derivatives, Bioorg Med Chem., vol. 20, No. 3, Feb. 1, 2012, pp. 1213-1221.
Tucker et al., Discovery of 3-{5-[(6-amino-1H-pyrazolo[3,4-b]pyridine-3-yl)methoxy]-2-chlorophenoxy)-5-chlorobenzonitrile (MK-4965): a potent, orally bioavailable HIV-1 non-nucleoside reverse transcriptase inhibitor with improved potency against key mutant viruses, J. Med. Chem., vol. 51, No. 20, Oct. 1, 2008, pp. 6503-6511.
Tucker et al., The design and synthesis of diaryl ether second generation HIV-1 non-nucleoside reverse transcriptase inhibitors (NNRTIs) with enhanced potency versus key clinical mutations, Bioorganic & Medicinal Chemistry Letters, vol. 18, No. 9, May 1, 2008, pp. 2959-2966.
Yang et al., Novel dengue virus-specific NS2B/NS3 protease inhibitor, BP2109, discovered by a high-throughput screening assay, Antimicrob Agents Chemotherapy, vol. 55, No. 1, Jan. 2011, pp. 229-238.
Yang et al., Synthesis of Chromones via Palladium-Catalyzed Ligand-Free Cyclocarbonylation of o-Iodophenols with Terminal Acetylenes in Phosphonium Salt Ionic Liquids, J. Org. Chem., vol. 75, 2010, pp. 948-950.
Yusof et al., Purified NS2B/NS3 serine protease of dengue virus type 2 exhibits cofactor NS2B dependence for cleavage of substrates with dibasic amino acids in vitro, J Biol Chem., vol. 275, No. 14, Apr. 7, 2000, pp. 9963-9969.
Zandi et al., Antiviral activity of four types of bioflavonoid against dengue virus type-2, Virology Journal, vol. 8:560, 2011, pp. 1-11.

(56) References Cited

OTHER PUBLICATIONS

Zhao et al., Novel indole-3-sulfonamides as potent HIV non-nucleoside reverse transcriptase inhibitors (NNRTIs), Bioorganic & Medicinal Chemistry Letters, vol. 18, No. 2, Jan. 15, 2008, pp. 554-559.
Zhou et al., A Selective Transformation of Flavanones to 3-Bromoflavones and Flavones Under Microwave Irradiation, Advanced Synthesis & Catalysis, vol. 348, No. 1-2, Jan. 2006, pp. 63-67.
Office Action, Mexican Patent Application No. MX/A/2015/005098, dated Nov. 1, 2018, 7 pages.

* cited by examiner

No treatment dilution    x 100000    x 10000    x 1000

*FIG. 3A*

Compound III 20 uM    15uM    10uM

Compound V

FLAVIVIRUS PROTEASE INHIBITORS

CROSS-REFERENCE TO PRIORITY APPLICATION

This application claims priority to U.S. Provisional Application No. 61/717,221, filed Oct. 23, 2012, which is incorporated herein by reference in its entirety.

STATEMENT REGARDING FEDERALLY FUNDED RESEARCH

This invention was made with government support under grant numbers 3R01AI070791, 3R01AI070791-03S1, and U01AI082068 awarded by the National Institutes of Health. The government has certain rights in the invention.

BACKGROUND

The mosquito-borne dengue virus serotypes 1-4 (DENV1-4) are included in the National Institute of Allergy and Infectious Disease (NIAID) list of Category A, B, or C emerging human pathogens along with yellow fever virus (YFV), West Nile virus (WNV), and Japanese encephalitis virus (JEV). DENVs cause serious illnesses associated with considerable morbidity and mortality. According to World Health Organization estimates, globally over 50 million people suffer from the symptoms of dengue fever annually, and of these at least 250,000 cases develop into dengue hemorrhagic fever (DHF) or dengue shock syndrome (DSS) resulting in considerable mortality, particularly among children in South Asian Countries. The World Health Organization estimates that 2.5 billion people (~40% of the world's population) live in areas that have increased risk of contracting dengue virus infections. Frequent outbreaks occur in the Americas including the continental U.S., mainly in the Southern states as well as in Puerto Rico and Hawaii. There is neither a vaccine nor antiviral therapeutic currently available for human use.

SUMMARY

Methods of treating or preventing *Flavivirus* infections in a subject are provided. The methods comprise administering to the subject a therapeutically effective amount of a *Flavivirus* inhibitor. A method of treating or preventing a *Flavivirus* infection in a subject described herein includes administering to the subject an effective amount of a compound selected from the group consisting of the following structures:

or a pharmaceutically acceptable salt thereof;

or a pharmaceutically acceptable salt thereof;

or a pharmaceutically acceptable salt thereof;

or a pharmaceutically acceptable salt thereof;

or a pharmaceutically acceptable salt thereof;

or a pharmaceutically acceptable salt thereof; and or a pharmaceutically acceptable salt thereof.

Optionally, the *Flavivirus* is the West Nile Virus, Dengue Virus serotype DENV-1, Dengue Virus serotype DENV-2, Dengue Virus serotype DENV-3, Dengue Virus serotype DENV-4, or Japanese Encephalitis Virus.

The method can further comprise administering a second compound or composition, wherein the second compound or composition includes an antiviral compound. Optionally, the second compound or composition is a protease inhibitor.

Also described herein are methods of inhibiting a *Flavivirus* protease in a cell (e.g., a host cell). The methods of inhibiting a *Flavivirus* protease in a cell include contacting a cell with an effective amount of a compound as described herein. Optionally, the *Flavivirus* protease is DENV-2 protease or WNV protease. Optionally, the contacting is performed in vivo or in vitro.

The details of one or more embodiments are set forth in the description and drawings below. Other features, objects, and advantages will be apparent from the description and drawings, and from the claims.

DESCRIPTION OF DRAWINGS

FIGS. 3A and 3B contain pictures of plaque assays performed to evaluate the anti-dengue viral activity of Compounds III and V.

FIGS. 4A, 4B, and 4C contain pictures of plaque assays performed to evaluate the anti-dengue viral activity of Compounds I, II, IV, VI, and VII.

DETAILED DESCRIPTION

Methods of treating a *Flavivirus* infection in a subject comprising administering to the subject a therapeutically effective amount of *Flavivirus* inhibitors, e.g., *Flavivirus* protease inhibitors, are disclosed. The *Flavivirus* inhibitors are administered in an effective amount to prevent or treat *Flavivirus* infections such as, for example, West Nile Virus, Dengue Virus, and Japanese Encephalitis Virus.

I. Compounds

A *Flavivirus* inhibitor useful in the methods described herein comprises
Compound I:

or a pharmaceutically acceptable salt thereof;
Compound II:

or a pharmaceutically acceptable salt thereof;
Compound III:

or a pharmaceutically acceptable salt thereof;
Compound IV:

or a pharmaceutically acceptable salt thereof;

Compound V:

or a pharmaceutically acceptable salt thereof;
Tolcapone, as represented by Compound VI:

or a pharmaceutically acceptable salt thereof; or
Tannic acid, as represented by Compound VII:

II. Pharmaceutical Formulations

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyethylene glycol (PEG), and PLURONICS™ (BASF; Florham Park, N.J.).

Compositions containing the compound described herein or derivatives thereof suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers, such as cocoa butter, polyethyleneglycol or a suppository wax, which are solid at ordinary temperatures but liquid at body temperature and, therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught therein.) Administration of the compounds and compositions described herein or pharmaceutically acceptable salts thereof can be carried out using therapeutically effective amounts of the compounds and compositions described herein or pharmaceutically acceptable salts thereof as described herein for periods of time effective to treat a disorder. The effective amount of the compounds and compositions described herein or pharmaceutically acceptable salts thereof as described herein may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

III. Methods of Making the Compounds

The compounds described herein can be prepared in a variety of ways known to one skilled in the art of organic 
synthesis. The compounds can be synthesized using synthetic methods known in the art of synthetic organic chemistry or variations thereon as appreciated by those skilled in the art. The compounds described herein can be prepared from readily available starting materials. Optimum reaction conditions may vary with the particular reactants or solvent used, but such conditions can be determined by one skilled in the art by routine optimization procedures.

Variations on Compound I, Compound II, Compound III, Compound IV, Compound V, Compound VI, and Compound VII include the addition, subtraction, or movement of the various constituents as described for each compound. Similarly, when one or more chiral centers is present in a molecule the chirality of the molecule can be changed. Additionally, compound synthesis can involve the protection and deprotection of various chemical groups. The use of protection and deprotection, and the selection of appropriate protecting groups can be readily determined by one skilled in the art. The chemistry of protecting groups can be found, for example, in Wuts and Greene, Protective Groups in Organic Synthesis, $4^{th}$ Ed., Wiley & Sons, 2006, which is incorporated herein by reference in its entirety. The synthesis and subsequent testing of various compounds as described by Compound I, Compound II, Compound III, Compound IV, Compound V, Compound VI, and Compound VII to determine efficacy is contemplated.

Reactions to produce the compounds described herein can be carried out in solvents, which can be readily selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

Optionally, the compounds described herein can be obtained from commercial sources. The compounds can be obtained from, for example, Alfa Aesar (Ward Hill, Mass.); ChemBridge Corporation (San Diego, Calif.); ChemDiv (San Diego, Calif.); and Waterstone Technology (Carmel, Ind.).

IV. Methods of Use

The methods described herein are useful for treating viral infections, such as *Flavivirus* infections, in humans, e.g., including pediatric and geriatric populations, and animals, e.g., veterinary applications. The methods described herein comprise administering to a subject a therapeutically effective amount of the compounds described herein or a pharmaceutically acceptable salt or prodrug thereof *Flavivirus* infections include, for example, West Nile Virus, Dengue Virus, and Japanese Encephalitis Virus. Several serotypes of Dengue Virus have been identified such as, for example, serotype DENV-1, serotype DENV-2, serotype DENV-3, and serotype DENV-4.

The methods described herein are useful for both prophylactic and therapeutic treatment of *Flavivirus* infections. For prophylactic use, a therapeutically effective amount of the compounds described herein are administered to a subject prior to exposure (e.g., before or when traveling to a location where *Flavivirus* infections are possible), during a period of potential exposure to *Flavivirus* infections, or after a period of potential exposure to *Flavivirus* infections. Prophylactic administration can occur for several days to weeks prior to potential exposure, during a period of potential exposure, and for a period of time, e.g., several days to weeks, after potential exposure. Therapeutic treatment involves administering to a subject a therapeutically effective amount of the compounds described herein after a *Flavivirus* infection is diagnosed.

In the methods described herein, a *Flavivirus* infection, for example, can be further treated with one or more additional agents. Optionally, the additional agent includes an antiviral agent. Optionally, the additional agent includes a protease inhibitor. The one or more additional agents and the compounds described herein or a pharmaceutically acceptable salt or prodrug thereof can be administered in any order, including simultaneous administration, as well as temporally spaced order of up to several days apart. The methods may also include more than a single administration of the one or more additional agents and/or the compounds described herein or a pharmaceutically acceptable salt or prodrug thereof. The administration of the one or more additional agent and the compounds described herein or a pharmaceutically acceptable salt or prodrug thereof may be by the same or different routes and concurrently or sequentially.

The methods described herein are also useful in inhibiting a *Flavivirus* protease in a cell (e.g., a host cell). Optionally, the *Flavivirus* protease can be DENV-2 protease. Optionally, the *Flavivirus* protease can be WNV protease. The method of inhibiting a *Flavivirus* protease in a cell includes contacting a cell with an effective amount of one or more compounds as described herein. Optionally, the contacting is performed in vivo. Optionally, the contacting is performed in vitro.

V. Kits

Also provided herein are kits for treating *Flavivirus* infections in a subject. A kit can include any of the compounds or compositions described herein. For example, a kit can include any of Compound I, Compound II, Compound III, Compound IV, Compound V, Compound VI, and Compound VII, or combinations thereof. A kit can further include one or more additional agents, such as a protease inhibitor. A kit can additionally include directions for use of the kit (e.g., instructions for treating a *Flavivirus* infection in a subject), a container, a means for administering the compounds or compositions (e.g., syringe, etc.), and/or a carrier.

As used herein the terms treatment, treat, or treating refer to a method of reducing or delaying one or more symptoms of a *Flavivirus* infection. Thus in the disclosed method, treatment can refer to a 10%, 20%, 30%, 40%, 50%, 60%, 70%, 80%, 90%, or 100% reduction in the severity or progression of one or more symptoms of the disease or condition. For example, a method for treating a disease is considered to be a treatment if there is a 10% reduction in one or more symptoms or signs of the *Flavivirus* infection in a subject as compared to a control. As used herein, control refers to the untreated condition. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder. For example, the method is considered to be a prevention if there is a reduction or delay in onset, incidence, severity, or recurrence of a *Flavivirus* infection. The reduction or delay in onset, incidence, severity, or recurrence of a *Flavivirus* infection can be a 10%, 20%, 30%, 40%, 50%, 60%, 70%, 80%, 90%, 100%, or any percent reduction in between 10% and 100% as compared to native or control levels.

As used herein, references to decreasing, reducing, or inhibiting include a change of 10%, 20%, 30%, 40%, 50%, 60%, 70%, 80%, 90% or greater as compared to a control level. Such terms can include, but do not necessarily include, complete elimination.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

Throughout this application, various publications are referenced. The disclosures of these publications in their entireties are hereby incorporated by reference into this application.

The examples below are intended to further illustrate certain aspects of the methods and compositions described herein, and are not intended to limit the scope of the claims.

EXAMPLES

Example 1

Protein Expression

DENV-2 and WNV proteases were expressed from 2 L cultures of TOP10F' cells (Invitrogen; Carlsbad, Calif.) transformed with expression plasmids pQE30-NS2BH(QR)-NS3pro and WNV clone 107, respectively. Cultures were grown in LB medium supplemented with ampicillin (100 μg/mL) and 0.1% glucose at 37° C. until the $OD_{600}$ reached 0.6-0.7. The medium was then replaced with fresh LB-ampicillin with 1 mM IPTG. Expression was done at 20° C. for 16 h. Cells were then pelleted and either frozen or used immediately for purification using a Talon metal affinity resin (Clontech; Mountain View, Calif.).

Example 2

High Throughput Screen (HTS)

A reaction mixture was prepared containing 200 mM Tris pH 9.5, 30% glycerol, 0.1% CHAPS detergent (to prevent non-specific aggregation of compounds), 50 nM DENV2QRpro enzyme and 10 μM Bz-Nle-Lys-Arg-Arg-AMC in each 30 μL reaction in duplicate 384-well plates. Aprotinin (2 μM) was used as a positive control. Compounds which inhibited the cleavage of the substrate by at least 50% were considered as positive hits. From the list of positive compounds, the highest scoring hits were selected for further analysis. Twenty nine compounds that consistently showed strong inhibition (>80%) at these concentrations (7 or 17 μg/mL) were chosen for a more extensive characterization. Out of the 29 compounds, only 22 dissolved in DMSO at 5 mM. The activities of the 22 compounds were tested against DENV-2 and WNV proteases at 10 and 25 μM of the inhibitor concentration. Those compounds that showed at least 50% inhibition at 10 μM were evaluated for their IC50s (Compounds I-VII). A control containing only 2% DMSO and the substrate was used to achieve the minimum value of relative fluorescence units (RFU) for background subtraction. Compounds that reduced the protease activity by ≥70% were selected for further analysis.

Example 3

In Vitro Protease Assay

Compound I, Compound II, Compound III, Compound IV, Compound V, Compound VI, and Compound VII were analyzed by in vitro protease assays. The compounds were tested for DENV-2 and WNV protease inhibition activity. All assays were done in triplicate in black 96-well plates. Protease activity experiments were performed in vitro using purified viral protease NS2B-N53-pro from DENV-2 or WNV. The reaction mixture of 100 μL/well contained 200 mM Tris pH 9.5, 30% glycerol, 27 nM WNV, 2% DMSO and fluorogenic tetra-peptide substrate Bz-Nle-Lys-Arg-Arg-AMC at concentrations that varied (0.05, 0.1, 0.5, 1, 2, 5, 10, and 25 μM). The percent activities after 30 min versus inhibitor concentration were plotted in GraphPad Prism v5.04 using the four-parameter nonlinear regression (Hill slope method).

In all assays, the inhibitor-enzyme complex was allowed to form by pre-incubation for 15 min at room temperature (RT) before addition of the substrate. After 5 min incubation, reactions were monitored by the release of free AMC, every 1.5 min for 30 min. The fluorescence emission was recorded at 465 nm following excitation at 385 nm using the Spectra Max Gemini EM (Molecular Devices; Silicon Valley, Calif.). The relative fluorescence units (RFU) were converted to absolute AMC product concentrations using Excel, where the data were transformed using the slope from the linear regression of the AMC calibration curve generated from the fluorescence values versus micromolar (μM) concentrations of free AMC. RFUs, obtained in a standard assay in the absence of inhibitors, were taken as 100% protease activity (or 0% inhibition), the background value (no protease) as 0% activity (or 100% inhibition). Kinetic values were determined using Microsoft Excel and GraphPad Prism 5 (La Jolla, Calif.). The activity data for the compounds are shown in Table 1.

TABLE 1

| Compound | % Inhib. DENV 2 Protease at | | % Inhib. WNV Protease at | | $IC_{50}$ (μM) | | cLogP | LE* |
|---|---|---|---|---|---|---|---|---|
| | 10 μM | 25 μM | 10 μM | 25 μM | DENV2 | WNV | | |
| I | 51 | 89 | 54 | 95 | 10.5 (±0.3) | 9.0 (±0.5) | 1.8 | 0.26 |
| II | 57 | 92 | 45 | 92 | 8.8 (±0.2) | 9.7 (±0.3) | 3.0 | 0.29 |
| III | 96 | 94 | 98 | 98 | 3.4 (±0.7) | 1.3 (±0.1) | 4.4 | 0.32 |
| IV | 63 | 82 | 71 | 95 | 8.5 (±0.1) | 6.7 (±0.4) | 3.9 | 0.29 |

TABLE 1-continued

| Compound | % Inhib. DENV 2 Protease at | | % Inhib. WNV Protease at | | $IC_{50}$ (µM) | | cLogP | LE* |
| --- | --- | --- | --- | --- | --- | --- | --- | --- |
| | 10 µM | 25 µM | 10 µM | 25 µM | DENV2 | WNV | | |
| V | 75 | 86 | 75 | 95 | 4.8 (±0.6) | 4.3 (±0.2) | 2.9 | 0.25 |
| VI | 90 | 92 | 99 | 67 | 0.758 (±0.05) | 0.680 (±0.11) | 2.9 | 0.42 |
| VII | 99 | 101 | 98 | 96 | 0.768 (±0.02) | 0.312 (±0.01) | N/A | N/A |

*LE represents ligand efficiency.

Compound III and Compound V were further tested for DENV-1, DENV-3, and DENV-4 protease inhibition activity.

TABLE 2

| Compound | DENV1 | DENV3 | DENV4 |
| --- | --- | --- | --- |
| III | 5.99 ± 1.4 | 4.8 ± 1.1 | 3.92 ± 0.05 |
| V | 6.4 ± 1.2 | 5.0 ± 1.4 | 5.32 ± 0.6 |

The data demonstrate that the compounds display broad spectrum flaviviral protease inhibition activity against several *Flavivirus* subgroups and also against different serotypes of DENV.

Example 4

DENV2 and WNV Replicon assay

The efficacy of the compounds was also examined in cell-based assays performed in mammalian cells. Mammalian cells are the host for replication of the virus; a compound added to the growth medium of the mammalian cell in which a replicon RNA or dengue virus is replicating, the compound of interest could permeate the cell and interfere with the replication process. If there is a quantitative readout of replication efficiency, the potency of the inhibitor compound could be evaluated in a quantifiable manner. There are two types of quantifiable assays available both employing mammalian cells; the first is the Baby Hamster Kidney (BHK) or monkey kidney (Vero) cells harboring DENV-2 or WNV replicon RNA, respectively, in a continuously replicating state and these are "stable replicon-expressing" cells. The second assay is infectivity assays in which mammalian cells are infected with DENV and the compound of interest is added at various concentrations and incubated. The inhibition of infectivity of the virus by the compound is measured by the extent of reduction of the titer of virus determined by plaque assay.

Figure 1:
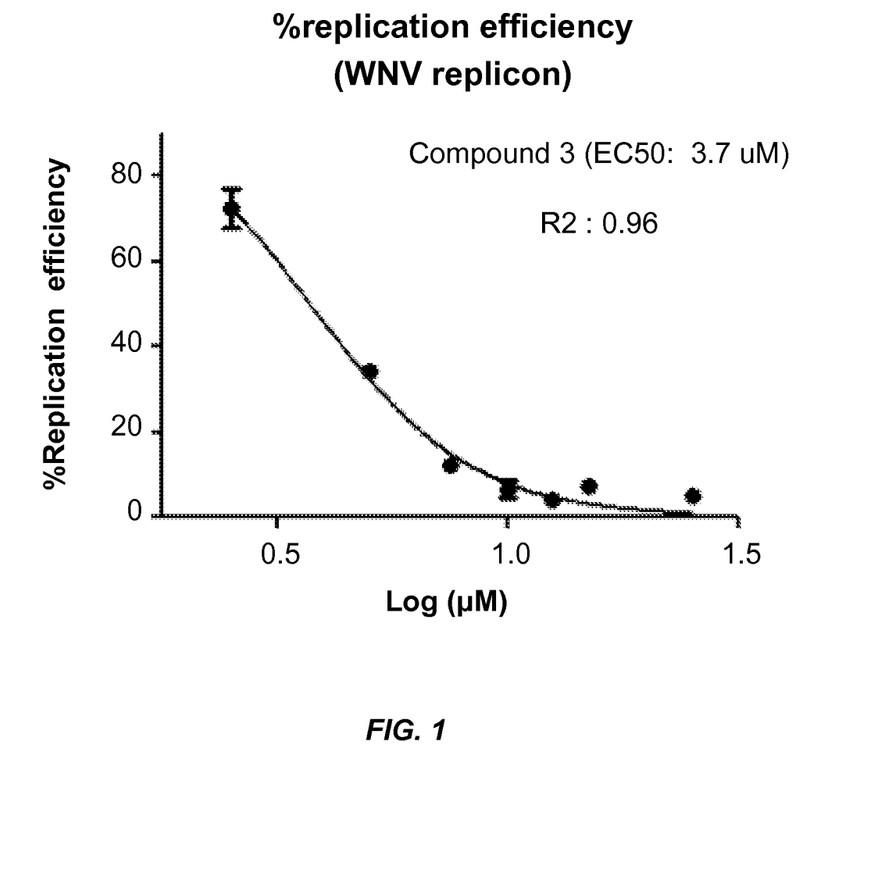
FIG. 1 is a plot demonstrating the $EC_{50}$ determination of Compound III using WNV replicon-expressing Vero cells.

Both drug efficacy and cytotoxicity were measured using the same experimental plate. Prior to compound treatment, BHK21-DENV2 or Vero-WNV cells at ~5×10$^4$ cells/100 µl were plated in 96-well plates with each well containing 10$^4$ cells. After 24 h incubation, the medium was replaced with 100 µL fresh medium containing different compound concentrations (0.5, 1, 2, 5, 10, and 25 µM) in triplicate wells. Cells were incubated again for 24 h. Cells were then washed with PBS and the luminescence signal from *Renilla* luciferase activity was read using the *Renilla* luciferase assay kit (Promega Corp; Fitchburg, Wis.) using a luminometer (Berthold Technologies, Inc.; Oak Ridge, Tenn.). Cell viability ($CC_{50}$) was measured as amount of ATP production in viable (live) cells using a chemiluminescence detection method (CellTiter Glo kit from Promega Corp) using the Model LB960 luminometer (Berthold Technologies). The $EC_{50}$ and $CC_{50}$ values of selected compounds were calculated similar to $IC_{50}$s using GraphPad Prism v5. Experiments were done in duplicates. FIG. 1 shows the $EC_{50}$ of Compound III as determined using the WNV replicon-expressing Vero cells. Table 3 shows the $EC_{50}$ and $CC_{50}$ values of Compound III and Compound V using WNV replicon-expressing Vero cells.

TABLE 3

| Compound ID | $EC_{50}$ (µM) | $CC_{50}$ (µM) | Therapeutic index (TI) |
| --- | --- | --- | --- |
| Compound III | 3.7 (range 3.4-3.9) | 130 (range 74-227) | 35 |
| Compound V | 9.7 (range 7.6-12.3) | 168 (143-198) | 17 |

Figure 2:
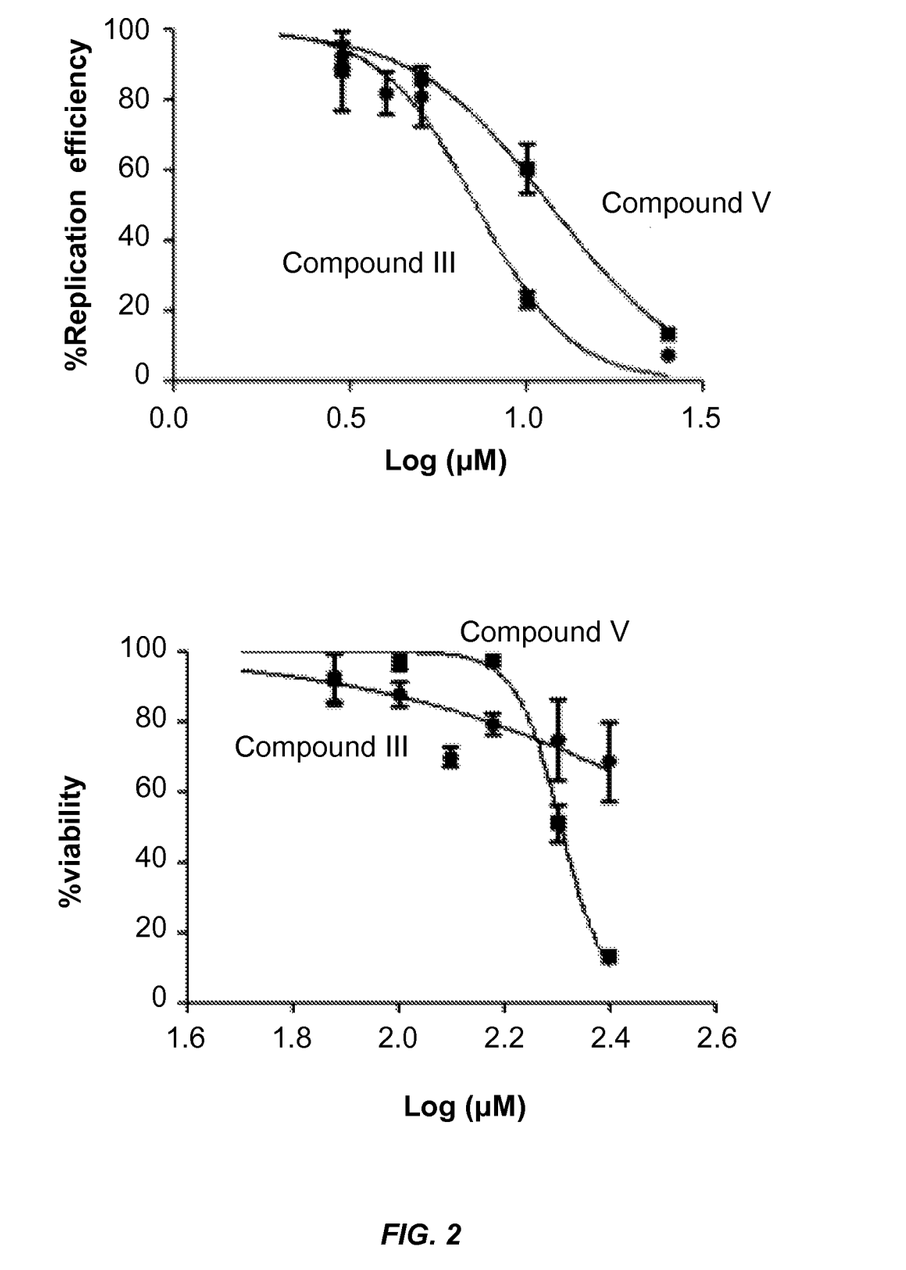
FIG. 2 contains plots demonstrating the $EC_{50}$ (top panel) and $CC_{50}$ (bottom panel) determinations of Compound III and Compound V.

Following a similar protocol, the $EC_{50}$ and $CC_{50}$ values of Compounds III and V for inhibition of DENV2 replicon-expressing BHK21 cells and cell viability of those cells treated with Compounds III and V were determined. The data are shown in Table 4 and FIG. 2.

TABLE 4

| Compound ID | $EC_{50}$ (µM) | $CC_{50}$ (µM) | Therapeutic index (TI) |
| --- | --- | --- | --- |
| Compound III | 7.2 | 407 | 56 |
| Compound V | 11.7 | 202 | 17 |

Example 5

Plaque Assays for Evaluating the Anti-Dengue Viral Activity

Figure 3A:
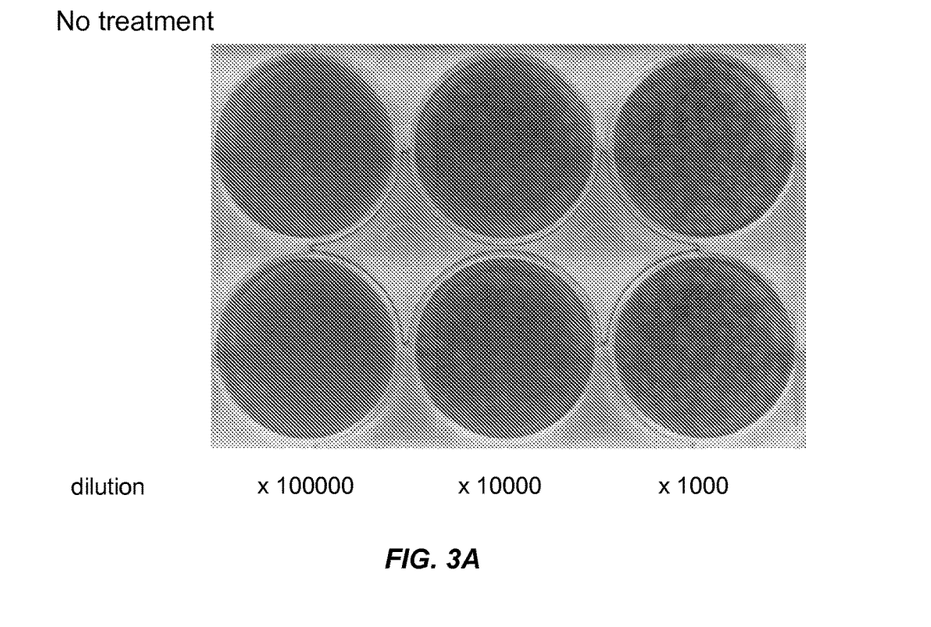
FIG. 3A represents the control where no compound was added.
Figure 3B:
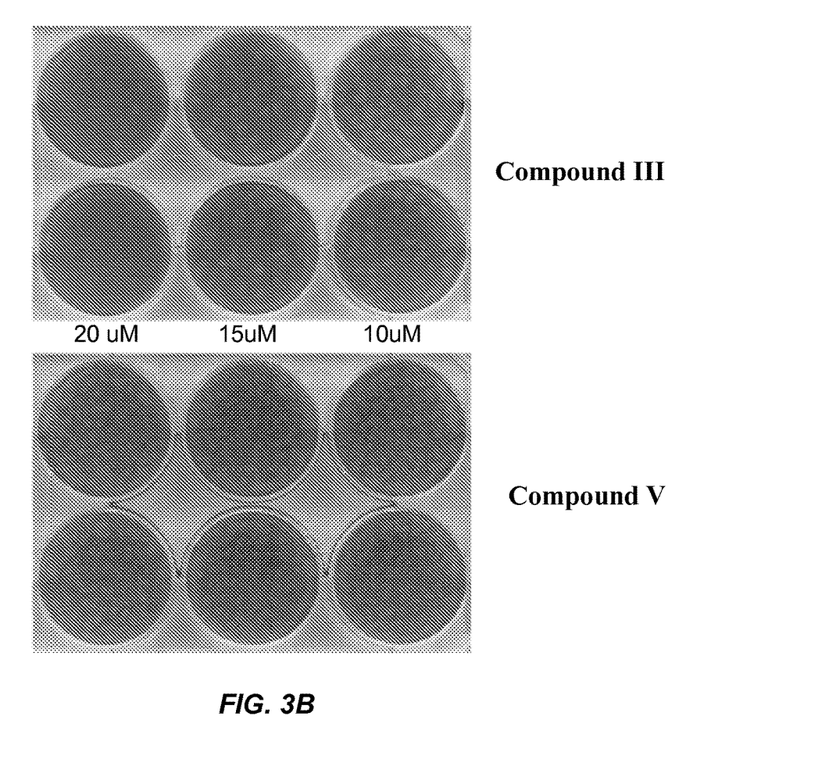
FIG. 3B shows the addition of 10 µM, 15 µM, and 20 µM of Compound III and Compound V.

BHK 21 cells (1×10$^5$) were plated onto each well of 12 well-cell culture plate. Five hours later, the medium was changed to opti-MEM and the compounds (Compound III and Compound V) were added with various concentrations (10, 15, and 20 µM). One hour later, the Dengue virus was added (MOI:1). After an additional 48 hours, the supernatant was collected and tested by the plaque assay. The data from the plaque assays is shown in FIG. 3A (no compound treatment) and FIG. 3B (treatment with various concentrations of Compound III and Compound V). The no-treatment sample data showed that the virus titer in the opti-MEM incubation for 48 hours is 2×10$^5$ PFU/ml (FIG. 3A). When Compound III was added at 20 µM, the virus titer was reduced to 2×10$^3$ (100× fold reduction). At 15 µM, the titer was reduced to 4×10$^4$ (a 5-fold reduction). At 10 µM, the titer was reduced to 6×10$^4$ (a 3.3-fold reduction). Thus, the EC50 in virus replication in vivo is less than 10 µM (FIG. 3B, top panel). In contrast, the inhibitory effect by Compound V was not observed in this range (10-20 µM) (FIG. 3B, bottom panel).

Figure 4A:
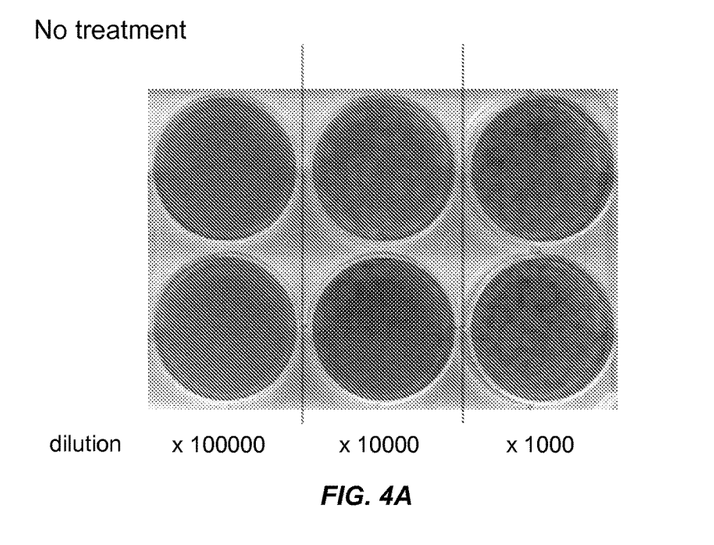
FIG. 4A represents the control where no compound was added.

LLC-MK2 cells were plated at 2.5×10⁵ cells per well in 6-well plates containing 2 ml culture medium and incubated overnight. Serially diluted supernatants from BHK21 cells treated with compounds at different concentrations as described above were incubated with cells in paired wells of six-well plates for 2 h. Cells were overlaid with 1× media containing 0.5% Sea-Kem GTG agarose (FMC Bioproducts; Philadelphia, Pa.) and were incubated for 7 days at 37° C. and visualized by staining with 0.01% neutral red solution overnight. The no-treatment control data showed that the virus titer for 48 hours incubation is 3×10⁵ PFU/ml (see FIG. 4A).

Figure 4B:
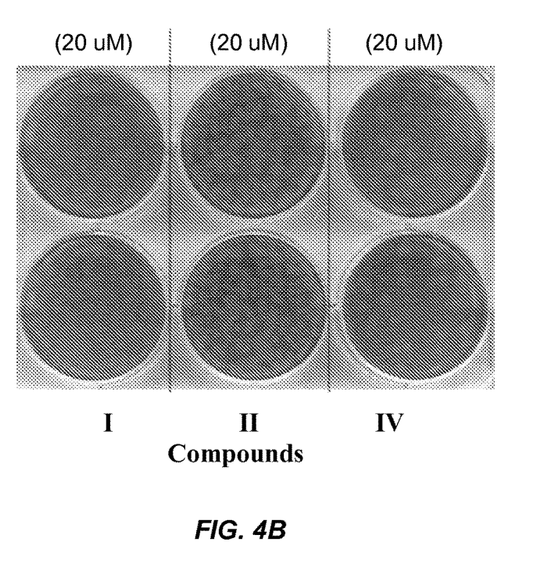
FIG. 4B shows the addition of 20 µM of Compounds I, II, and IV.
Figure 4C:
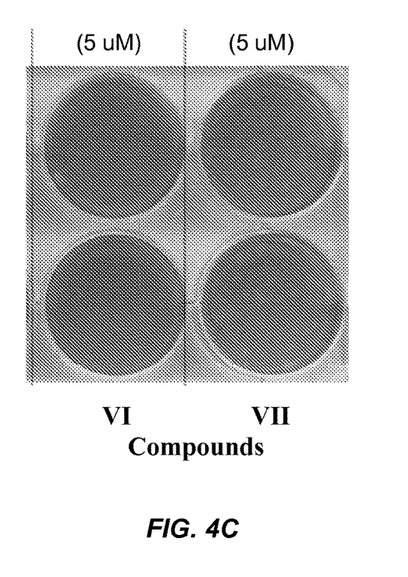
FIG. 4C shows the addition of 5 µM of Compounds VI and VII.

The potencies of Compounds I, II, IV, VI, and VII were also analyzed by plaque assay. Compounds I and II did not show a significant inhibition of the virus titer at 20 μM concentration (FIG. 4B). Compound IV diminished the virus titers more than 10-fold at 20 μM. Thus, the $EC_{50}$ in virus replication in vivo is less than 20 μM (FIG. 4B). Compound VI showed greater than 100-fold reduction of the virus titer at 5 μM, showing that EC50 is significantly less than 5 μM (FIG. 4C). Compound VII showed more than 10 times diminished virus titer at 5 μM, demonstrating that the $EC_{50}$ is below 5 μM (FIG. 4C).

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods are intended to fall within the scope of the appended claims. Thus a combination of steps, elements, components, or constituents may be explicitly mentioned herein; however, all other combinations of steps, elements, components, and constituents are included, even though not explicitly stated.

What is claimed is:

1. A method of treating a *Flavivirus* infection in a subject, comprising administering to the subject a therapeutically effective amount of a compound selected from the group consisting of:

or a pharmaceutically acceptable salt thereof,
wherein the compound inhibits a *Flavivirus* protease.

2. The method of claim 1, wherein the *Flavivirus* is the West Nile Virus.

3. The method of claim 1, wherein the *Flavivirus* is Dengue Virus serotype DENV-1.

4. The method of claim 1, wherein the *Flavivirus* is Dengue Virus serotype DENV-2.

5. The method of claim 1, wherein the *Flavivirus* is Dengue Virus serotype DENV-3.

6. The method of claim 1, wherein the *Flavivirus* is Dengue Virus serotype DENV-4.

7. The method of claim 1, wherein the *Flavivirus* is Japanese Encephalitis Virus.

8. The method of claim 1, further comprising administering a second compound or composition, wherein the second compound or composition includes an antiviral compound.

9. The method of claim 8, wherein the second compound or composition is a protease inhibitor.

10. A method of inhibiting a *Flavivirus* protease in a cell, comprising:

contacting a cell with an effective amount of a compound selected from the group consisting of:

-continued or a pharmaceutically acceptable salt thereof.

11. The method of claim 10, wherein the *Flavivirus* protease is DENV-2 protease.

12. The method of claim 10, wherein the *Flavivirus* protease is WNV protease.

13. The method of claim 10, wherein the contacting is performed in vivo.

14. The method of claim 10, wherein the contacting is performed in vitro.

* * * * *